US009820482B2

(12) United States Patent
Bingham et al.

(10) Patent No.: US 9,820,482 B2
(45) Date of Patent: *Nov. 21, 2017

(54) COMPOSITIONS AND METHODS WITH EFFICACY AGAINST SPORES AND OTHER ORGANISMS

(71) Applicant: GOJO INDUSTRIES, INC., Akron, OH (US)

(72) Inventors: James Edmund Bingham, Akron, OH (US); David R. Macinga, Stow, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/009,004

(22) Filed: Jan. 28, 2016

(65) Prior Publication Data

US 2016/0143274 A1 May 26, 2016

Related U.S. Application Data

(63) Continuation of application No. 14/615,552, filed on Feb. 6, 2015, now Pat. No. 9,277,749.

(60) Provisional application No. 61/936,945, filed on Feb. 7, 2014, provisional application No. 62/067,068, filed on Oct. 22, 2014.

(51) Int. Cl.
| | |
|---|---|
| *A01N 31/02* | (2006.01) |
| *A01N 47/44* | (2006.01) |
| *A01N 37/04* | (2006.01) |
| *A01N 43/16* | (2006.01) |
| *A01N 37/02* | (2006.01) |
| *A01N 47/28* | (2006.01) |
| *A01N 59/00* | (2006.01) |
| *C11D 3/20* | (2006.01) |
| *C11D 3/48* | (2006.01) |
| *C11D 7/26* | (2006.01) |

(52) U.S. Cl.
CPC ............ *A01N 31/02* (2013.01); *A01N 37/02* (2013.01); *A01N 37/04* (2013.01); *A01N 43/16* (2013.01); *A01N 47/28* (2013.01); *A01N 47/44* (2013.01); *A01N 59/00* (2013.01); *C11D 3/2003* (2013.01); *C11D 3/48* (2013.01); *C11D 7/261* (2013.01)

(58) Field of Classification Search
CPC ........ A01N 31/02; A01N 37/02; A01N 37/04; A01N 43/16; A01N 47/28; A01N 47/44; A01N 59/00; C11D 3/2003; C11D 3/48; C11D 7/261
USPC ........................................................ 514/565
See application file for complete search history.

(56) References Cited

U.S. PATENT DOCUMENTS

| | | |
|---|---|---|
| 3,968,248 A | 7/1976 | Boucher |
| 3,983,252 A | 9/1976 | Buchalter |
| 4,518,585 A | 5/1985 | Greene et al. |
| 4,557,898 A | 12/1985 | Greene et al. |
| 4,691,043 A | 9/1987 | Demarne et al. |
| 4,900,721 A | 2/1990 | Bansemir et al. |
| 4,927,638 A | 5/1990 | Bykadi et al. |
| 4,946,868 A | 8/1990 | Demarne et al. |
| 4,956,170 A | 9/1990 | Lee |
| 4,983,635 A | 1/1991 | Martin |
| 5,062,979 A | 11/1991 | Scharf et al. |
| 5,219,887 A | 6/1993 | Andrews et al. |
| 5,236,614 A | 8/1993 | Jacquet et al. |
| 5,284,875 A | 2/1994 | Martin |
| 5,322,856 A | 6/1994 | Martin |
| 5,378,731 A | 1/1995 | Andrews et al. |
| 5,380,756 A | 1/1995 | Andrews et al. |
| 5,436,008 A | 7/1995 | Richter et al. |
| 5,490,980 A | 2/1996 | Richardson et al. |
| 5,492,932 A | 2/1996 | Kundsin |
| 5,569,691 A | 10/1996 | Guggenberger et al. |
| 5,620,655 A | 4/1997 | Nevermann |
| 5,631,218 A | 5/1997 | Allan et al. |
| 5,728,404 A | 3/1998 | von Rheinbaben et al. |
| 5,749,924 A | 5/1998 | Murch et al. |
| 5,767,054 A | 6/1998 | Sprugel et al. |
| 5,767,163 A | 6/1998 | Kundsin |
| 5,783,146 A | 7/1998 | Williams, Jr. |
| 5,800,827 A | 9/1998 | Igarashi et al. |
| 5,830,488 A | 11/1998 | Suzuki et al. |
| 5,891,392 A | 4/1999 | Monticello et al. |

(Continued)

FOREIGN PATENT DOCUMENTS

| | | |
|---|---|---|
| EP | 2070552 A1 | 6/2009 |
| GB | 1539771 | 2/1979 |
| WO | 0194513 A1 | 12/2001 |
| WO | 02059244 A2 | 8/2002 |
| WO | WO2006096148 | 9/2006 |
| WO | WO2009050447 | 4/2009 |
| WO | 2009117299 A2 | 9/2009 |

(Continued)

OTHER PUBLICATIONS

International Search Report and Written Opinion of the International Searching Authority; PCT/US2015/014728, dated May 20, 2015.
David p. Elder; et al., "Antimicrobial Preservatives Part Two: Choosing a Perservative", American Pharmaceutical Review, Jan. 1, 2012.

*Primary Examiner* — Kristin Vajda
(74) *Attorney, Agent, or Firm* — Calfee, Halter & Griswold LLP

(57) ABSTRACT

Compositions and methods for the disinfection of surfaces are provided. The compositions include at least about 40 weight percent of a $C_{1-6}$ alcohol, and a primary enhancer selected from protein denaturants. The disinfectant composition is characterized by a pH of less than about 3. Broad spectrum efficacy is achieved, and synergistic activity is exhibited against *C. difficile* spores.

12 Claims, 5 Drawing Sheets

(56) References Cited

U.S. PATENT DOCUMENTS

| | | |
|---|---|---|
| 5,914,302 A | 6/1999 | Murch et al. |
| 5,985,929 A | 11/1999 | Kern |
| 6,001,864 A | 12/1999 | Akashi et al. |
| 6,042,818 A | 3/2000 | Bragulla et al. |
| 6,106,774 A | 8/2000 | Monticello et al. |
| 6,123,966 A | 9/2000 | Kross |
| 6,238,682 B1 | 5/2001 | Klofta et al. |
| 6,248,343 B1 | 6/2001 | Jampani et al. |
| 6,358,906 B1 | 3/2002 | Ochs et al. |
| 6,423,868 B1 | 7/2002 | Carr et al. |
| 6,488,942 B1 | 12/2002 | Ingemann |
| 6,554,620 B1 | 4/2003 | Iwai |
| 6,583,176 B2 | 6/2003 | Arata |
| 6,627,207 B1 | 9/2003 | Petersen |
| 6,667,289 B2 | 12/2003 | Harrison et al. |
| 6,803,057 B2 | 10/2004 | Ramirez et al. |
| 7,005,451 B1 | 2/2006 | Nevermann et al. |
| 7,041,631 B2 | 5/2006 | Ochs et al. |
| 7,192,601 B2 | 3/2007 | Walker |
| 7,214,651 B2 | 5/2007 | Mohr et al. |
| 7,294,609 B2 | 11/2007 | Saito et al. |
| 7,700,533 B2 | 4/2010 | Egbe et al. |
| 7,745,384 B2 | 6/2010 | Perry et al. |
| 7,824,665 B2 | 11/2010 | Miyamoto et al. |
| 7,985,773 B2 | 7/2011 | Greten et al. |
| 8,034,844 B2 | 10/2011 | Fox et al. |
| 8,388,991 B2 | 3/2013 | Sondgeroth |
| 8,481,480 B1 | 7/2013 | Lann et al. |
| 9,277,749 B2 * | 3/2016 | Bingham ............... A01N 37/02 |
| 2001/0009891 A1 | 7/2001 | Murch et al. |
| 2001/0014652 A1 | 8/2001 | Murch et al. |
| 2001/0036963 A1 | 11/2001 | Behrends et al. |
| 2002/0045666 A1 | 4/2002 | Russo et al. |
| 2002/0090343 A1 | 7/2002 | Moore et al. |
| 2002/0103098 A1 | 8/2002 | Harrison et al. |
| 2002/0119574 A1 | 8/2002 | Berg |
| 2002/0123523 A1 | 9/2002 | Arata |
| 2002/0142051 A1 | 10/2002 | Rochon |
| 2002/0192297 A1 | 12/2002 | Ramirez et al. |
| 2003/0099717 A1 | 5/2003 | Cabrera |
| 2003/0180377 A1 | 9/2003 | Ramirez et al. |
| 2003/0198689 A1 | 10/2003 | Arata |
| 2004/0023822 A1 | 2/2004 | Ochs et al. |
| 2004/0043912 A1 | 3/2004 | Murch et al. |
| 2004/0058878 A1 | 3/2004 | Walker |
| 2004/0171687 A1 | 9/2004 | Kemp et al. |
| 2004/0242443 A1 | 12/2004 | Murch et al. |
| 2005/0003994 A1 | 1/2005 | Ochs et al. |
| 2005/0058719 A1 | 3/2005 | Ramirez et al. |
| 2005/0238728 A1 | 10/2005 | Evans |
| 2005/0274624 A1 | 12/2005 | Arata |
| 2006/0019855 A1 | 1/2006 | Saito et al. |
| 2006/0094638 A1 | 5/2006 | Mohr et al. |
| 2006/0178281 A1 | 8/2006 | Alasri |
| 2006/0193745 A1 | 8/2006 | Arndt et al. |
| 2006/0285995 A1 | 12/2006 | Hobbs et al. |
| 2006/0292196 A1 | 12/2006 | Padiurashvili et al. |
| 2007/0027119 A1 | 2/2007 | Ahmed et al. |
| 2007/0053942 A1 | 3/2007 | Nishibayashi et al. |
| 2007/0059380 A1 | 3/2007 | Ramirez et al. |
| 2007/0184016 A1 | 8/2007 | Macinga et al. |
| 2007/0238652 A1 | 10/2007 | Kokai-Kun et al. |
| 2007/0258915 A1 | 11/2007 | Kielbania |
| 2007/0269530 A1 | 11/2007 | Arata et al. |
| 2007/0274926 A1 | 11/2007 | Fuis et al. |
| 2007/0275929 A1 | 11/2007 | Fuis et al. |
| 2007/0280901 A1 | 12/2007 | Fuis et al. |
| 2007/0281999 A1 | 12/2007 | Fox et al. |
| 2008/0045491 A1 | 2/2008 | Fitchmun |
| 2008/0138438 A1 | 6/2008 | Taylor et al. |
| 2008/0139656 A1 | 6/2008 | Taylor et al. |
| 2008/0199535 A1 | 8/2008 | Taylor et al. |
| 2008/0249187 A1 | 10/2008 | Ali et al. |
| 2008/0286223 A1 | 11/2008 | Fuls et al. |
| 2008/0305182 A1 | 12/2008 | Ramirez et al. |
| 2008/0317799 A1 | 12/2008 | Baker et al. |
| 2009/0012174 A1 | 1/2009 | Seitz, Jr. et al. |
| 2009/0061017 A1 | 3/2009 | Pedersen et al. |
| 2009/0176887 A1 | 7/2009 | Vlasaty et al. |
| 2009/0197786 A1 | 8/2009 | Perry et al. |
| 2009/0252775 A1 | 10/2009 | Arndt et al. |
| 2009/0291944 A1 | 11/2009 | Ash et al. |
| 2010/0003343 A1 | 1/2010 | Ramirez et al. |
| 2010/0143496 A1 | 6/2010 | Larson et al. |
| 2010/0151046 A1 | 6/2010 | Okamoto et al. |
| 2010/0159028 A1 | 6/2010 | Shultz |
| 2010/0204323 A1 | 8/2010 | Theiler et al. |
| 2010/0240600 A1 | 9/2010 | Shimamoto et al. |
| 2010/0240752 A1 | 9/2010 | Drellinger et al. |
| 2010/0261792 A1 | 10/2010 | Neas et al. |
| 2010/0286009 A1 | 11/2010 | Vierbaum et al. |
| 2010/0323895 A1 | 12/2010 | Garner |
| 2010/0324135 A1 | 12/2010 | Arata |
| 2010/0330196 A1 | 12/2010 | Ramirez et al. |
| 2011/0009484 A1 | 1/2011 | Arata et al. |
| 2011/0027399 A1 | 2/2011 | Shimamoto et al. |
| 2011/0081300 A1 | 4/2011 | Awad |
| 2011/0135702 A1 | 6/2011 | Hoffman et al. |
| 2011/0182958 A1 | 7/2011 | Omidbakhsh |
| 2011/0245219 A1 | 10/2011 | Ionidis |
| 2012/0018445 A1 | 1/2012 | Mendoza et al. |
| 2012/0125377 A1 | 5/2012 | Perlman et al. |
| 2012/0128719 A1 | 5/2012 | Baker, Jr. et al. |
| 2012/0141600 A1 | 6/2012 | Taylor et al. |
| 2012/0213835 A1 | 8/2012 | Neas et al. |
| 2012/0230869 A1 | 9/2012 | Ramirez et al. |
| 2012/0276219 A1 | 11/2012 | Taylor et al. |
| 2012/0301556 A1 | 11/2012 | Norton |
| 2013/0018097 A1 | 1/2013 | Boldue et al. |
| 2013/0023582 A1 | 1/2013 | Shimamoto et al. |
| 2013/0037048 A1 | 2/2013 | Edgington et al. |
| 2013/0089533 A1 | 4/2013 | Zhu et al. |
| 2013/0095184 A1 | 4/2013 | Lyczak et al. |
| 2013/0142856 A1 | 6/2013 | Worthington et al. |
| 2013/0150313 A1 | 6/2013 | Flury et al. |
| 2013/0184267 A1 | 7/2013 | Ash et al. |
| 2013/0210767 A1 | 8/2013 | Garner |
| 2014/0011766 A1 | 1/2014 | Krafft |
| 2014/0024688 A1 | 1/2014 | Callahan et al. |
| 2014/0041686 A1 | 2/2014 | Ryther et al. |
| 2014/0134224 A1 | 5/2014 | Mallet et al. |

FOREIGN PATENT DOCUMENTS

| | | |
|---|---|---|
| WO | WO2010035008 | 4/2010 |
| WO | WO2010127231 | 11/2010 |
| WO | WO2011036628 | 3/2011 |

* cited by examiner

COMPOSITIONS AND METHODS WITH EFFICACY AGAINST SPORES AND OTHER ORGANISMS

RELATED APPLICATIONS

This application is a continuation of U.S. patent application Ser. No. 14/615,552, filed Feb. 6, 2015, which claims the benefit of U.S. Provisional Patent Application Ser. No. 61/936,945, filed Feb. 7, 2014, and U.S. Provisional Patent Application Ser. No. 62/067,068, filed Oct. 22, 2014, both of which are incorporated herein by reference.

TECHNICAL FIELD

Embodiments of the present invention provide compositions and methods having efficacy against spores such as *Clostridium difficile* spores, and other organisms. Acidified disinfectant compositions containing one or more enhancers exhibit synergistic efficacy against spores such as *C. difficile* spores, and also exhibit excellent efficacy against fungi, bacteria, and viruses.

BACKGROUND OF THE INVENTION

Patients in healthcare facilities can sometimes contract serious infections. Such infections may be generally referred to as healthcare-associated infections (HAIs). While most types of HAIs are declining, one infection, caused by the bacteria *Clostridum difficile* (*C. difficile*), remains at historically high levels. *C. difficile* is a spore-forming, Gram-positive anaerobic *bacillus* of the human intestine and is thought to be present in 2-5% of the adult population. Pathogenic *C. difficile* strains produce multiple toxins, the most well-characterized of which are enterotoxin (*Clostridium difficile* toxin A) and cytotoxin (*C. difficile* toxin B), both of which can produce diarrhea and inflammation in infected patients. The emergence of a new, highly toxic strain of *C. difficile*, resistant to flouroquinolone antibiotics, such as ciprofloxacin and levofloxacin have also been reported. *C. difficile* infection causes diarrhea and other intestinal problems and is linked to 14,000 deaths in the United States each year.

Control of *C. difficile* outbreaks present significant challenges to health care facilities. *C. difficile* spores survive routine environmental cleaning with detergents and hand hygiene with alcohol-based gels. The spores can survive on surfaces for long periods of time. As a result, the bacteria can be cultured from almost any surface. Once spores are ingested, their acid-resistance allows them to pass through the stomach unscathed. They germinate and multiply into vegetative cells in the colon upon exposure to bile acids.

A variety of strategies have been proposed to kill *C. difficile* spores on various surfaces, with limited success. Bleach-based compositions have been employed for hard surfaces, and have been shown to reduce the environmental burden of *C. difficile*. but can be corrosive. Hydrogen peroxide-based compositions have also been proposed, including combinations of hydrogen peroxide and peracetic acid, a combination of hydrogen peroxide and silver cation dry-mist system, and the so-called Accelerated Hydrogen Peroxide (AHP). Peracids generally have poor stability and corrosive properties. Hydrogen peroxide is also prone to decomposition, and concentrated solutions can be highly corrosive. Alcohol-based sanitizers have not generally been effective. In fact, ethanol is sometimes used to store *C. difficile* spores.

A need remains for more stable, less corrosive compositions having good efficiency against *C. difficile* spores.

Spores and other pathogenic infectious agents such as bacteria, fungi, viruses, fungal and bacterial spores, and conformationally altered prions can be resistant to current sanitizers and cleansers. Chemical and biological warfare agents can be fast-acting and pervasive. There is a continuing need for effective, easy to use products that will be safe for humans and the environment, that can decontaminate skin, and particularly wounds, following chemical and/or biological warfare agent exposure, that can decontaminate surfaces to eliminate infectious agents such as conformationally altered prions, bacteria, fungi, viruses, and fungal and bacterial spores, and that can be used to decontaminate homes, building materials, and furniture that has been infected with black mold spores, and that can reduce the transmission of infectious pathogens.

DETAILED DESCRIPTION OF ILLUSTRATIVE EMBODIMENTS

Figure 1:
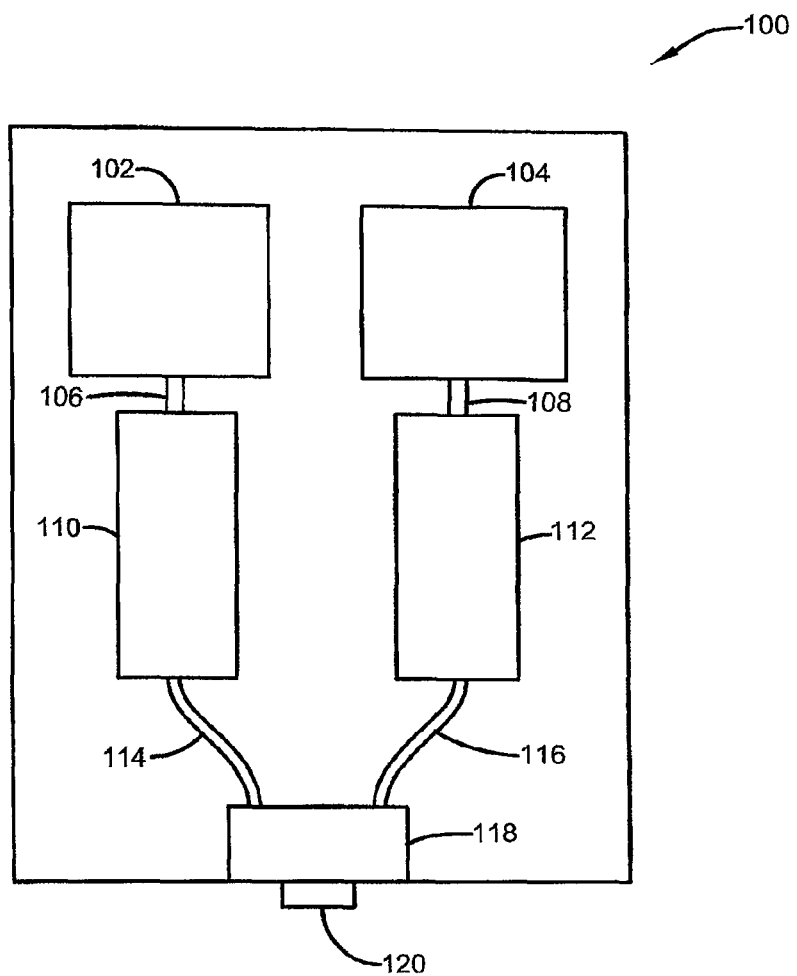
FIG. 1 is a schematic view of a dispenser according to the present invention.

In one or more embodiments, the present invention provides disinfectant compositions. The physical form of the disinfectant composition is not particularly limited, and in one or more embodiments, the composition may be presented as a liquid that is poured, pumped, sprayed, or otherwise dispensed, a gel, an aerosol, or a foam, including both aerosol and non-aerosol foams. The disinfectant composition of the present invention may be employed on a wide variety of surfaces or substrates, including hard surfaces, soft surfaces, non-living (inanimate) surfaces, living tissue, skin, soil, porous, and non-porous surfaces. For purposes of this specification, the term "surface" should be understood to include skin. The compositions of the invention may be employed to disinfect or otherwise sanitize inanimate objects such as instruments, medical equipment, furniture, handrails, textiles, etc. In one or more embodiments, the disinfectant composition may be presented as a wipe, i.e. a tissue or cloth that is wiped over a surface.

The disinfectant compositions comprise at least one $C_{1-6}$ alcohol, i.e. an alcohol containing 1 to 6 carbon atoms. Such alcohols may be referred to as lower alkanols. In one or more embodiments, the disinfectant compositions comprise at least one $C_{1-4}$ alcohol. Examples of lower alkanols include, but are not limited to, methanol, ethanol, propanol, butanol, pentanol, hexanol, and isomers and mixtures thereof. In one or more embodiments, the alcohol comprises ethanol, propanol, or butanol, or isomers or mixtures thereof. In one or more embodiments, the alcohol comprises isopropanol. In other embodiments, the alcohol comprises ethanol. In one or more embodiments, the disinfectant compositions comprise a mixture of alcohols. In one or more embodiments, the disinfectant compositions comprise a mixture of ethanol and isopropanol. In one or more embodiments, the disinfectant compositions comprise butanol. In one or more embodiments, the disinfectant compositions comprise a mixture of ethanol and butanol. In one or more embodiments, the disinfectant compositions comprise a mixture of n-butanol and isopropanol.

In one or more embodiments, the disinfectant composition comprises at least about 40 percent by weight (wt. %) alcohol, based upon the total weight of the disinfectant composition. In one or more embodiments, the disinfectant composition comprises at least about 45 wt. %, in other embodiments, at least about 50 wt. % alcohol, in other embodiments, at least about 55 wt. %, in other embodiments, the disinfectant composition comprises at least about 60 wt. % alcohol, in other embodiments, the disinfectant composition comprises at least about 65 wt. % alcohol, in yet other embodiments, the disinfectant composition comprises at least about 70 wt. % alcohol, and in still yet other embodiments, the disinfectant composition comprises at least about 75 wt. % alcohol, based upon the total weight of disinfectant composition.

In one embodiment, the disinfectant composition comprises less than about 99 wt. % alcohol, in other embodiments, the disinfectant composition comprises less than about 98 wt. % alcohol, in other embodiments, the disinfectant composition comprises less than about 95 wt. % alcohol. In one embodiment, the disinfectant composition comprises less than about 90 wt. % alcohol, in other embodiments, the disinfectant composition comprises less than about 85 wt. % alcohol, in other embodiments, the disinfectant composition comprises less than about 80 wt. % alcohol. More or less alcohol may be required in certain instances, depending particularly on other ingredients and/or the amounts thereof employed in the composition.

In one or more embodiments, the disinfectant composition comprises from about 40 wt. % to about 99 wt. % alcohol, in other embodiments, from about 45 wt. % to about 98 wt. % alcohol, in other embodiments, the disinfectant composition comprises from about 50 wt. % to about 95 wt. % of alcohol, based upon the total weight of the disinfectant composition. In one or more embodiments, the disinfectant composition comprises from about 40 wt. % to about 90 wt. % alcohol, in other embodiments, from about 45 wt. % to about 85 wt. % alcohol, in other embodiments, the disinfectant composition comprises from about 50 wt. % to about 85 wt. % of alcohol, in other embodiments, from about 50 wt. % to about 85 wt. %, in yet other embodiments, the disinfectant composition comprises from about 60 wt. % to about 78 wt. % of alcohol, and in still other embodiments, the disinfectant composition comprises from about 65 wt. % to about 75 wt. % of alcohol, based upon the total weight of the disinfectant composition.

In any of the above embodiments, the disinfectant composition may include one or more enhancers. Advantageously, the composition includes at least one primary enhancer that potentiates the efficacy of the disinfectant composition. Examples of primary enhancers include protein denaturants. Examples of primary enhancers include chaotropic agents. Examples of primary enhancers include amine-containing enhancers, α-aminoacids, salts of alkali metals, salts of alkaline earth metals, and anionic surfactants.

In any of the above embodiments, the disinfectant composition may include an amine-containing enhancer. Examples of amine-containing enhancers include urea, thiourea, dimethyl urea, guanidine-HCl, guanidine thiocyanate, aminoguanidine bicarbonate, guanidine carbonate, guanidine phosphate, L-NG-nitroarginine, and aminoguanidine-HCL. In one or more of the above embodiments, the enhancer comprises urea. In one or more of the above embodiments, the enhancer comprises guanidine-HCl. In one or more of the above embodiments, the enhancer comprises aminoguanidine-HCl.

In any of the above embodiments, the disinfectant composition may include an α-aminoacid. Examples of α-aminoacids include sulfur-containing aminoacids and nitro-containing aminoacids. Examples of sulfur-containing aminoacids include L-cysteine and methionine. Examples of nitro-containing aminoacids include L-NG-nitroarginine. Examples of α-aminoacids include α-aminoacid chelators. Examples of α-aminoacid chelators include the trisodium salt of methylglycinediacetic acid ($Na_3MGDA$). $Na_3MGDA$ is commercially available under the trade name Trilon M from BASF.

Interestingly, not all chelators are primary enhancers. For example, acrylic acid/acrylamidomethyl propane sulfonic acid copolymer, which is sold under the tradename CG4500 by Lubrizol Corporation, and is known to have chelating ability, does not work as a primary enhancer. That is, acrylic acid/acrylamidomethyl propane sulfonic acid copolymer does not exhibit a synergistic enhancement of the efficacy of alcohol against *C. difficile* spores, even at a pH of less than 3. However, such chelators as acrylic acid/acrylamidomethyl propane sulfonic acid copolymer may enhance the efficacy against *C. difficile* spores, when combined with a C1-6 alcohol and a primary enhancer at a pH of no more than 3.

In any of the above embodiments, the disinfectant composition may include one or more salts of alkali metals and alkaline earth metals. Examples of salts include ammonium calcium, iron, lithium, magnesium, and sodium salts. Examples of salts include ammonium chloride, ammonium iron citrate, calcium chloride, iron perchlorate, lithium perchlorate, lithium acetate, magnesium chloride, sodium chlorate, sodium chloride, sodium chlorite, and tris-HCl (tris is 2-Amino-2-hydroxymethyl-propane-1,3-diol).

In any of the above embodiments, the disinfectant composition may include one or more anionic surfactants. Anionic surfactants include sodium lauryl sulfate (SLS) (also known as sodium dodecyl sulfate (SDS)) and sodium laureth sulfate (SLES).

Combinations of primary enhancers may also be employed. In one or more embodiments, the disinfectant composition comprises $Na_3MGDA$ and sodium chloride. In one or more embodiments, the disinfectant composition comprises urea and sodium nitrite. In one or more embodiments, the disinfectant composition comprises urea and SDS. In one or more embodiments, the disinfectant composition comprises urea and SLES.

Advantageously, a synergistic sporicidal effect is observed when the enhancer is combined with alcohol at an acidic pH. In certain embodiments, enhancers that exhibit little or no efficacy on their own against *C. difficile* spores provide an enhanced efficacy when combined with alcohol according to the present invention, and a further enhanced efficacy when the pH of the disinfectant composition is less than 3. It has surprisingly been found that, while disinfectant compositions show little or no efficacy against the spores, the combination of an enhancer and alcohol at a low pH exhibits synergistically enhanced efficacy against *C. difficile* spores.

The amount of enhancer is not particularly limited, so long as it is at least an efficacy-enhancing amount. The minimum amount of enhancer that corresponds to an efficacy-enhancing amount can be determined by comparing the log kill of spores achieved by a composition comprising an alcohol to a composition comprising an alcohol and a given amount of enhancer. The amount of enhancer below which no difference in log kill is seen is an efficacy-enhancing amount. In other words, rapid sporicidal efficacy is observed at lower concentrations of alcohol when an enhancer is present compared to when the enhancer is not present.

In one or more embodiments, the amount of primary enhancer is no more than about 15 wt. %, in other embodiments, no more than about 10 wt. %, in other embodiments, no more than about 8 wt. %, in other embodiments, no more than about 5 wt. %, in other embodiments, no more than about 3 wt. %, in other embodiments, no more than about 2 wt. %, in other embodiments, no more than about 1 wt. %, in other embodiments, no more than about 0.5 wt. %, based upon the total weight of the disinfecting composition.

In one or more embodiments, the amount of primary enhancer is greater than about 0.1 wt. %, in other embodiments, greater than about 0.5 wt. %, in other embodiments, greater than about 1 wt. %, in other embodiments, greater than about 2 wt. %, in other embodiments, greater than about 3 wt. %, in other embodiments, greater than about 5 wt. %, in other embodiments, greater than about 8 wt. %, based upon the total weight of the disinfecting composition.

In one embodiment, the enhancer is added in an amount of from about 0.1 to about 20 wt. %, based upon the total weight of the disinfectant composition. In another embodiment, the amount of enhancer is from about 0.25 to about 15 wt. %, and in yet another embodiment, from about 0.5 to about 12 wt. %, based upon the total weight of the disinfectant composition. It will be understood that greater levels of enhancer can be used, if desired, and are expected to perform equally as well. It will be understood that when a combination of primary enhancers is employed, the amount of each primary enhancer may be reduced.

In one or more embodiments, the pH of the disinfectant composition is less than about 3, in other embodiments, less than or equal to about 2.75, in other embodiments, less than or equal to about 2.5, in other embodiments, less than or equal to about 2.3, in other embodiments, less than or equal to about 2, in other embodiments, the pH is 1.8 or less, in other embodiments, the pH is 1.6 or less, in other embodiments, the pH is 1.5 or less. In one or more embodiments, the pH of the disinfectant composition is from about 0 to about 2.75. In one or more embodiments, the pH of the disinfectant composition from about 0.1 to about 2. In one or more embodiments, the pH of the disinfectant composition from about 0.5 to about 1.8. In one or more of the above embodiments, the pH of the disinfectant composition from about 1 to about 1.5. The disinfectant composition may therefore be referred to as acidified, since the disinfectant composition has an acidic pH.

The disinfectant composition may be acidified by the addition of one or more acids. The type of acid is not limited, however, weak acids are not preferred. The acid should have a pKa of 5.4 (the pKa of citric acid) or less.

Examples of useful acidifying agents include mineral acids and organic acids. Mineral acids include, without limitation, hydrochloric acid, nitric acid, phosphoric acid, phosphonic acid, boric acid, and sulfuric acid. Organic acids include sulfonic acids, organophosphorus acids, carboxylic acids such as benzoic acids, propionic acids, phthalic acids, butyric acids, acetic acids, amino acids, and other substituted and unsubstituted organic acids.

Examples of organic acids include adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxoglutaric acid, dl-glyceric acid, and 2,5 furandicarboxylic acid.

It has been found that, in certain embodiments, acidifying the disinfectant composition enhances the efficacy of the alcoholic solutions against *C. difficile*.

In any of the above embodiments, the disinfectant composition may include one or more secondary enhancers that, when a primary enhancer is present in combination with alcohol at a low pH, further enhance the efficacy of the composition. Surprisingly, the secondary enhancers do not significantly enhance the efficacy of the alcohol unless a primary enhancer is also present. In one or more embodiments, the secondary enhancer provides the benefit of maintaining good efficacy at a pH higher than for compositions that do not include a secondary enhancer.

Examples of secondary enhancers include non-ionic surfactants, such as decyl glucoside and polyalkoxylated dimethicones including PEG-12 dimethicone. Examples of secondary enhancers also include organic acids, such as citric acid, lauric acid, tannic acid, ascorbic and iodoacetic acid. Examples of secondary enhancers include also include auxiliary antimicrobial agents. Examples of secondary enhancers include also include oxidizing agents such as sodium nitrite. Examples of secondary enhancers include sugars and sugar alcohols. Examples of secondary enhancers include monosaccharides such as fructose. In one or more embodiments, the secondary enhancer includes glycerol.

In one or more embodiments, the amount of secondary enhancer in the disinfectant composition is zero. In one or more embodiments, the amount of secondary enhancer is no more than about 10 wt. %, in other embodiments, no more than about 8 wt. %, in other embodiments, no more than about 5 wt. %, in other embodiments, no more than about 3 wt. %, in other embodiments, no more than about 2 wt. %, in other embodiments, no more than about 1 wt. %, in other embodiments, no more than about 0.5 wt. %, based upon the total weight of the disinfecting composition.

In one or more embodiments, the amount of secondary enhancer is greater than about 0.1 wt. %, in other embodiments, greater than about 0.5 wt. %, in other embodiments, greater than about 1 wt. %, in other embodiments, greater than about 2 wt. %, in other embodiments, greater than about 3 wt. %, in other embodiments, greater than about 5 wt. %, in other embodiments, greater than about 8 wt. %, based upon the total weight of the disinfecting composition.

Examples of auxiliary antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethyl hexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidi amide; 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, tropolone, $C_{6-10}$-alkane diols such as hexanediol, octanediol, and decanediol, and mixtures thereof. In one or more embodiments, the about of auxiliary antimicrobial agent is from about 0.1 to about 1 wt. %, based upon the total weight of the disinfectant composition. In one or more embodiments, the auxiliary antimicrobial agent is selected from benzalkonium chloride and chlorhexidine gluconate.

The composition can further comprise a wide range of optional ingredients, with the proviso that they do not deleteriously affect the sanitizing efficacy of the composition. By deleterious is meant that the decrease in the log reduction is not de minimus, or in other words, the log reduction of *C. difficile* spores does not decrease by more than about 0.5. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, foam surfactants, fragrance components, humectants, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

It has been discovered that the combination of alcohol and enhancer at low pH exhibits enhanced antimicrobial efficacy. Advantageously, auxiliary antimicrobials, some of which can be harsh on skin, are not required. In certain embodiments, the disinfectant composition does not contain any auxiliary antimicrobial ingredients. Any antimicrobial ingredient other than the combination of alcohol, enhancer and acid may be referred to as an auxiliary antimicrobial agent. In one or more embodiments, the amount of auxiliary antimicrobial agent (including preservatives) is less than about 1 wt. %, in other embodiments, less than about 0.5 wt. %, in other embodiments, less than about 0.25 wt. %, based upon the total weight of the disinfectant composition. In one or more embodiments, the amount of auxiliary antimicrobial agent (including preservatives) is less than about 0.1 wt. %, in other embodiments, less than about 0.05 wt. %, in other embodiments, less than about 0.01 wt. %, based upon the total weight of the disinfectant composition. In another embodiment, the disinfectant composition is devoid of auxiliary antimicrobial agents.

Advantageously, certain ingredients that have been designated as critical to current sporicidal compositions can be limited in the disinfectant composition of the present invention. For example, hypochlorous acid and precursors thereof are not necessary, and can be limited, if desired, to less than about 0.5 wt. %, or in another embodiment to less than about 0.1 wt. %, based upon the total weight of the disinfectant composition. In another embodiment, the disinfectant composition is devoid of hypochlorous acid.

In one or more embodiments, the amount of peroxyacids such as peracetic acid may be limited. When limited, in one or more embodiments, the amount of peroxyacid may be less than 0.125 wt. %, in other embodiments less than about 0.08 wt. %, based upon the total weight of the disinfectant composition. In another embodiment, the disinfectant composition is devoid of peroxyacid.

In one or more embodiments, the amount of peroxide may be limited, if desired, to less than about 0.5 wt. %, or other embodiments to less than about 0.1 wt. %, based upon the total weight of the disinfectant composition. In another embodiment, the disinfectant composition is devoid of peroxide.

Indeed, any component other than the alcohol, enhancer, acidifier, and optionally a secondary enhancer, is not necessary to achieve antimicrobial efficacy and can optionally be limited to less than about 0.5 wt. %, if desired to less than about 0.1 wt. %, if desired to less than about 0.01 wt. %, or if desired to less than about 0.001 wt. %. It will be understood that the balance of the disinfectant composition may, in certain embodiments, include water or other suitable solvent. In one embodiment, the disinfectant composition is devoid of any component other than alcohol, enhancer, acidifier, and optionally water or other suitable solvent.

The disinfectant composition may be prepared by simply mixing the components together. In one embodiment, where one or more components is obtained as a solid powder, the disinfectant composition may be prepared by a method comprising dispersing the solid powder in water or alcohol with slow to moderate agitation, and then adding other ingredients as desired, and mixing until the mixture is homogeneous.

In one embodiment, where the disinfectant composition is in liquid form, the percent solids of the disinfectant composition is less than about 6 percent, in another embodiment, less than about 5 percent, in yet another embodiment, less than about 4 percent, in still another embodiment, less than about 3 percent, in another embodiment, less than about 2 percent, in yet another embodiment, less than about 1 percent. The percent solids can be determined by various methods known in the art.

Advantageously, it has been found that compositions according to the present invention have efficacy against a broad spectrum of gram positive and gram negative bacteria, fungi, parasites, fungal and bacterial spores, enveloped and non-enveloped viruses, and prions (CJD, CWD, BSE, Scrapie). One or more embodiments of the present invention exhibit efficacy against one or more of spores of *Bacillus anthracis, Bacillus cereus, Clostridium difficile, Clostridium botulinum*, and *Clostridium tetani*.

Unexpectedly, when an enhancer is combined with alcohol at a low pH, according to the present invention, sporicidal activity is enhanced, i.e. potentiated. In one or more embodiments, the disinfectant composition is effective at killing *C. difficile* spores. In one or more embodiments, the disinfectant composition is also effective in killing gram negative and gram positive bacteria, fungi, parasites, non-enveloped and enveloped viruses. In one or more embodiments, the disinfectant composition has rapid antimicrobial efficacy against bacteria such as *Staphylococcus aureus*, methicillin-resistant *S. aureus, Escherichia coli, Pseudomonas aeruginosa, Serratia marcescens*, fungi such as *Candida albicans* and *Aspergillus niger*, and black mold spores *Stachybotrys chartanim*. In one or more embodiments, the disinfectant composition has rapid efficacy against skin microflora, including resident and transient skin microflora.

Thus, the present invention further provides a method for killing or inactivating microbes such as *C. difficile* spores on a surface comprising applying, to the surface, an effective amount of a disinfectant composition as described herein. The disinfectant composition may be employed on a wide variety of surfaces or substrates, including hard surfaces, soft surfaces, skin, non-skin, animate, inanimate, porous, and non-porous surfaces.

Unless otherwise specified, the term log reduction refers to $\log_{10}$ reduction. In one or more embodiments, the method provides a log reduction against spores of at least about 1 in less than about 1 minute. In other embodiments, the method provides a log reduction against spores of at least about 1.5 in less than about 1 minute. In yet other embodiments, the method provides a log reduction against spores of at least about 2 in less than about 1 minute. In other embodiments, the method provides a log reduction against spores of at least about 2.5 in less than about 1 minute. In yet other embodiments, the method provides a log reduction against spores of at least about 3 in less than about 1 minute.

In one or more embodiments, the method provides a log reduction against spores of at least about 1 in less than about 30 seconds. In other embodiments, the method provides a log reduction against spores of at least about 1.5 in less than about 30 seconds. In yet other embodiments, the method provides a log reduction against spores of at least about 2 in less than about 30 seconds. In other embodiments, the method provides a log reduction against spores of at least about 2.5 in less than about 30 seconds. In yet other embodiments, the method provides a log reduction against spores of at least about 3 in less than about 30 seconds.

In one or more embodiments, the method provides a log reduction against spores on inanimate, hard, non-porous surfaces of at least about 6 in 10 minutes or less. In other embodiments, the method provides a log reduction against spores of at least about 6 in about 7 minutes or less. In yet other embodiments, the method provides a log reduction against spores of at least about 6 in about 6 minutes or less. In other embodiments, the method provides a log reduction against *C. difficile* spores on inanimate, hard, non-porous surfaces of at least about 6 in about 10 minutes or less. In yet other embodiments, the method provides a log reduction against *C. difficile* spores on inanimate, hard, non-porous surfaces of at least about 6 in about 7 minutes or less. In yet other embodiments, the method provides a log reduction against *C. difficile* spores on inanimate, hard, non-porous surfaces of at least about 6 in about 6 minutes or less.

In one or more embodiments, the method provides a log reduction against *C. difficile* spores of at least about 1 in less than about 1 minute. In other embodiments, the method provides a log reduction against *C. difficile* spores of at least about 1.5 in less than about 1 minute. In yet other embodiments, the method provides a log reduction against *C. difficile* spores of at least about 2 in less than about 1 minute. In other embodiments, the method provides a log reduction against *C. difficile* spores of at least about 2.5 in less than about 1 minute. In yet other embodiments, the method provides a log reduction against *C. difficile* spores of at least about 3 in less than about 1 minute.

In one or more embodiments, the method provides a log reduction against *C. difficile* spores of at least about 1 in less than about 30 seconds. In other embodiments, the method provides a log reduction against *C. difficile* spores of at least about 1.5 in less than about 30 seconds. In yet other embodiments, the method provides a log reduction against *C. Difficile* spores of at least about 2 in less than about 30 seconds. In other embodiments, the method provides a log reduction against *C. difficile* spores of at least about 2.5 in less than about 30 seconds. In yet other embodiments, the method provides a log reduction against *C. difficile* spores of at least about 3 in less than about 30 seconds.

In one or more embodiments, the method provides a log reduction against *C. difficile* spores on skin of at least about 1 in less than about 1 minute. In other embodiments, the method provides a log reduction against *C. difficile* spores on skin of at least about 1.5 in less than about 1 minute. In yet other embodiments, the method provides a log reduction of *C. difficile* spores on skin of at least about 2 in less than about 1 minute. In other embodiments, the method provides a log reduction against *C. difficile* spores on skin of at least about 2.5 in less than about 1 minute. In yet other embodiments, the method provides a log reduction against *C. difficile* spores on skin of at least about 3 in less than about 1 minute.

In one or more embodiments, the method provides a log reduction against *C. difficile* spores on skin of at least about 1 in less than about 30 seconds. In other embodiments, the method provides a log reduction against *C. difficile* spores on skin of at least about 1.5 in less than about 30 seconds. In yet other embodiments, the method provides a log reduction against *C. difficile* spores on skin of at least about 2 in less than about 30 seconds. In other embodiments, the method provides a log reduction against *C. difficile* spores on skin of at least about 2.5 in less than about 30 seconds. In yet other embodiments, the method provides a log reduction against *C. difficile* spores on skin of at least about 3 in less than about 30 seconds.

The methods of the present invention include the step of applying an disinfectant composition to a surface.

Advantageously, good efficacy is achieved by the methods of the present invention when the disinfectant composition is applied to the surface at standard temperature and at close to standard pressure. In one or more embodiments, the temperature of the disinfectant composition when applied to the surface may be less than about 150° F., in other embodiments, less than about 120° F., and in other embodiments, less than about 105° F. In one or more embodiments, the temperature of the disinfectant composition may be in the range of from about 40° F. to about 150° F., in other embodiments in the range of from about 40° F. to about 105° F., and in other embodiments, in the range of about 70° F. to 105° F.

Although the liquid disinfectant compositions of the present invention may be applied to the surface to be cleaned by spraying, no high pressure application is required. During this step, the disinfectant composition may be brought into contact with the target surface in bursts or in a continuous manner by circulating, flooding, spraying, foaming or fogging. The step may also be carried out by forming a two phase annular mist of antimicrobial treatment solution and air.

Advantageously, the methods of the present invention provide good efficacy against spores within 10 minutes or less. Embodiments of the invention provide good efficacy against spores within 7 minutes or less. Embodiments of the invention provide good efficacy against spores within 6 minutes or less. Embodiments of the invention provide good efficacy against spores within 5 minutes or less. Embodiments of the invention provide good efficacy against spores within 2 minutes or less. Embodiments of the invention provide good efficacy against spores within 1 minute or less. Embodiments of the invention provide good efficacy against spores within 30 seconds or less. In any of the embodiments disclosed herein, the spores may include *C. difficile* spores. Advantageously, the methods of the present invention provide good efficacy against *C. difficile* spores within 5 minutes or less. Embodiments of the invention provide good efficacy against *C. difficile* spores within 2 minutes or less. Embodiments of the invention provide good efficacy against *C. difficile* spores within 1 minute or less. Embodiments of the invention provide good efficacy against *C. difficile* spores within 30 seconds or less. Thus, in one or more embodiments, the duration of contact of the disinfectant composition with the target surface is from about 20 seconds to 5 minutes, in other embodiments, from about 25 seconds to about 2 minutes, and in other embodiments, from about 30 seconds to about 1 minute. It will be understood that, in some embodiments, a longer contact time is advantageous, and in one or more embodiments, the contact time may be up to 30 minutes, and in other embodiments, up to about 60 minutes.

The amount of disinfectant composition to be applied to the target surface is not particularly limited. At a minimum, a sufficient amount of disinfectant composition should be applied to substantially wet the surface such that the surface will remain wet for the desired contact time, noting that there will be some evaporation of the disinfectant composition.

Any amount of the disinfectant composition may be used for each application, so long as it is at least an effective amount to contact substantially the entire target surface and keep it wet for a contact time of at least 30 to 60 seconds. In one or more embodiments, the amount of the disinfectant composition is sufficient to contact substantially the entire target surface and keep it wet for a contact time of at least 5 minutes. In one or more embodiments, the amount of the disinfectant composition is sufficient to contact substantially the entire target surface and keep it wet for a contact time of at least 6 minutes. In one or more embodiments, the amount of the disinfectant composition is sufficient to contact substantially the entire target surface and keep it wet for a contact time of at least 7 minutes. In one or more embodiments, the amount of the disinfectant composition is sufficient to contact substantially the entire target surface and keep it wet for a contact time of at least 10 minutes. In one or more embodiments, the amount of the disinfectant composition is sufficient to contact substantially the entire target surface and keep it wet for a contact time of at least 30 minutes. In one or more embodiments, the amount of the disinfectant composition is sufficient to contact substantially the entire target surface and keep it wet for at least 60 minutes.

In one or more embodiments, the sporicidal disinfectant composition may be prepared by combining two or more liquid pre-mix compositions. A first pre-mix composition may comprise a concentrate of the primary enhancer, and a second pre-mix composition may comprise a concentrate of the alcohol, such that combination of the pre-mix compositions results in an disinfectant composition comprising alcohol and a primary enhancer as described hereinabove.

In other embodiments, a first pre-mix composition may comprise a concentrate of the alcohol and primary enhancer, and the second pre-mix composition may comprise a diluent, such that combination of the pre-mix compositions results in an disinfectant composition comprising alcohol and a primary enhancer at the concentrations as described hereinabove.

The pre-mix components may be dispensed from physically separate packages or from a unitary package having non-communicating chambers. For purposes of this specification, the term dual dispenser apparatus refers to a configuration where multiple liquid components are dispensed from a plurality of physically separate packages, and also refers to a configuration where multiple liquid components are dispensed from a unitary package having a plurality of non-communicating chambers, each chamber having an orifice through which an aliquot of a component is dispensed.

In one or more embodiments, aliquots of the pre-mix components are dispensed substantially simultaneously, such that the liquid aliquots are commingled. In particular embodiments, the aliquots are dispensed through orifices that are configured to enable the commingling of the aliquots. It will be understood that the dispenser may take a variety of forms, and may include a variety of components and configurations in order to cause the desired comingling of aliquots of the pre-mix components and dispensing of a product.

One embodiment of an exemplary dispenser is shown in FIG. 1 and is generally indicated by the numeral 100. Dispenser 100 may include a first reservoir 102 containing a first liquid pre-mix component (e.g. concentrated primary enhancer pre-mix component), and a second reservoir 104 containing a second liquid pre-mix component (e.g. alcoholic diluent pre-mix component). The pH-adjusting agent may be present in either or both of the pre-mix components. As will be apparent to those skilled in the art, and as indicated above, the first and second reservoirs 102 and 104 are not in direct communication with one another, and the first and second pre-mix components are therefore stored separately within the dispenser. Although separate reservoirs are shown in FIG. 1, it is contemplated that the first and second reservoirs 102 and 104 may be provided as physically separate chambers in a single package. Each of the first and second reservoirs 102 and 104 is impervious to fluid transfer therethrough, except through inlet passages 106 and 108, respectively.

In one or more embodiments, the present invention provides a method of preparing an disinfectant composition, the method comprising the steps of providing a dispenser having a first reservoir containing a first liquid pre-mix, and a second reservoir containing a second liquid pre-mix, wherein the dispenser is adapted to dispense an aliquot of the first pre-mix and an aliquot of the second pre-mix, such that the aliquots commingle. Upon commingling, the aliquots of the first pre-mix and second pre-mix form an disinfectant composition comprising an alcohol and a primary enhancer at a pH of less than about 3.

In certain embodiments, a first pump 110 may be in fluid communication with the first reservoir 102 through the inlet passage 106, and a second pump 112 may be in fluid communication with the second reservoir 104 through the inlet passage 108. First and second pumps 110 and 112 may be any type of pump known to those skilled in the art and suitable for conveying the first and second liquid pre-mix components from the first and second reservoirs 102 and 104. In one or more embodiments, the pumps 110 and 112 may both be positive displacement pumps. The first and second pumps 110 and 112 discharge the first and second pre-mix components through outlet passages 114 and 116, respectively. In certain embodiments, the output or displacement of the first and second pumps 110 and 112 may be adjustable to vary the rate of fluid flow therethrough. While the exemplary dispenser 100 shown and described includes first and second pumps 110 and 112, it is also contemplated that a single pump may be used, and may be in fluid communication with both the first and second reservoirs 102 and 104.

The outlet passages 114 and 116 may each extend to a mixing nozzle 118 where the first and second pre-mix components are comingled to form an disinfectant composition. The features and dimensions of the mixing nozzle 118 may be adjusted to vary the volume of each pre-mix aliquot, as well as the rate of mixing and comingling of the first and second pre-mix components. The mixing nozzle 118 includes a dispensing passage 120 through which the disinfectant composition is dispensed.

In certain embodiments, the first and second pumps 110 and 112 may be adjusted to produce substantially the same flow rate of the first and second pre-mix components therethrough. In other embodiments, the pumps 110 and 112 may be adjusted to provide different flow rates, and in certain embodiments, the pre-mix components may be dispensed sequentially.

In certain embodiments, the first and second pumps 110 and 112 may be adjusted to select substantially the same aliquot volume for the first and second pre-mix components. In other embodiments, the pumps 110 and 112 may be adjusted to provide different aliquot volumes.

In one or more embodiments, the first and second pumps 110 and 112 may be adapted to dispense a single dose of composition upon actuation. In the same or other embodiments, the first and second pumps 110 and 112 may be adapted to produce a continuous flow of the disinfectant composition upon actuation.

In one or more embodiments, the first pre-mix may include a concentrated form of the compositions of the present invention, and the second pre-mix may include a diluent, such that upon being dispensed, the combination forms a composition that includes the amounts of components taught herein.

Advantageously, embodiments of the present invention provide easy to use products that are safe for humans and the environment, and that can decontaminate skin, and particularly wounds. Following chemical and/or biological warfare agent exposure, embodiments of the present invention can contain and/or destroy the agent, preventing cutaneous penetration and further contamination. Embodiments of the present invention can decontaminate surfaces to eliminate infectious agents such as conformationally altered prions, bacteria, fungi, viruses, and fungal and bacterial spores, and that can be used to decontaminate homes, building materials, and furniture that has been infected with black mold spores. Embodiments of the present invention can reduce the transmission of infectious pathogens.

In order to demonstrate the practice of the present invention, the following examples have been prepared and tested. The examples should not, however, be viewed as limiting the scope of the invention. The claims will serve to define the invention.

EXAMPLES

Example 1 was a solution of 70 wt. % ethanol in water, to which 12 N hydrochloric acid had been added to achieve a pH of about 1.5.

Example 2 was a solution of 5 wt. % urea in water, to which 12 N hydrochloric acid had been added to achieve a pH of about 1.5.

Example 3 was a solution of 70 wt. % ethanol and 5 wt. % urea in water, to which 12 N hydrochloric acid had been added to achieve a pH of about 1.5.

Example 4 was a solution of 70 wt. % ethanol in water, to which 12 N hydrochloric acid had been added to achieve a pH of about 5.

Example 5 was a solution of 5 wt. % urea in water, to which 12 N hydrochloric acid had been added to achieve a pH of about 5.

Example 6 was a solution of 70 wt. % ethanol and 5 wt. % urea in water, to which 12 N hydrochloric acid had been added to achieve a pH of about 5.

The samples were tested for efficacy against *C. difficile* spores, according to the ASTM E2783-11: "Standard Test Method for Assessment of Antimicrobial Activity for Water Miscible Compounds Using a Time-Kill Procedure."

Figure 2:
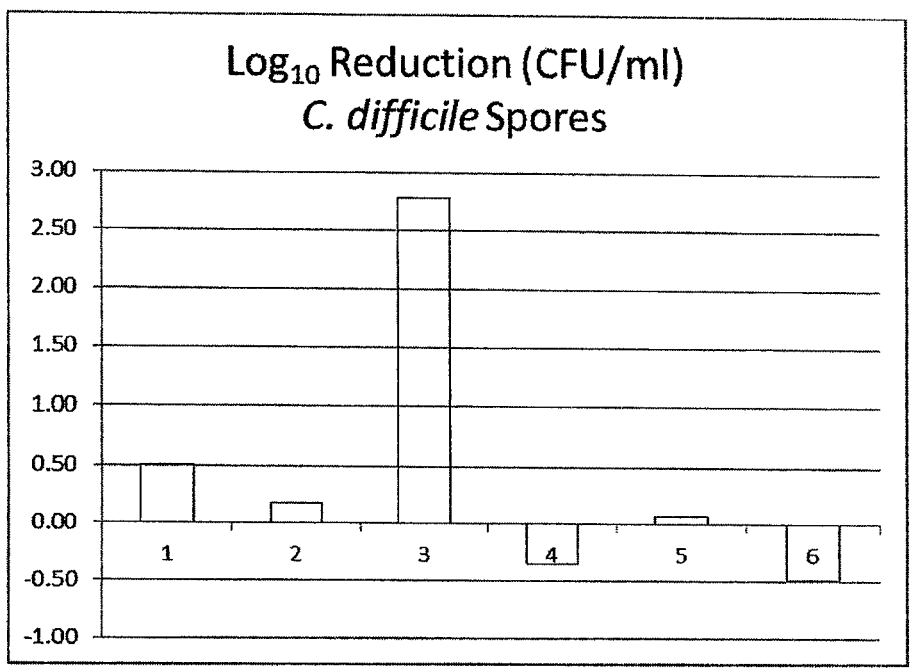
FIG. 2 is a graphical representation of log reduction (CFU/ml) against *C. difficile* spores for test compositions as described herein.

Contact time was 30 seconds. Temperature was room temperature. Results are shown in Table 1 and FIG. 2.

TABLE 1

| Example | Composition | pH | $Log_{10}$ Reduction *C. difficile* spores |
|---|---|---|---|
| 1 | 70% ethanol | 1.5 | 0.51 |
| 2 | 5% urea | 1.5 | 0.17 |
| 3 | 70% ethanol + 5% urea | 1.5 | 2.78 |
| 4 | 70% ethanol | 5.0 | −0.35 |
| 5 | 5% urea | 5.0 | 0.07 |
| 6 | 70% ethanol + 5% urea | 5.0 | −0.49 |

Similar results were achieved when samples were prepared and tested as described above, but varying the type of acid that was used to adjust the pH. Nitric acid, sulfuric acid, hydrochloric acid, hydrobromic acid, hydroiodic acid, and perchloric acid were tried instead of hydrochloric acid, and all gave similar results.

Example 7 was a solution of 70 wt. % ethanol in water, to which 12 N hydrochloric acid had been added to achieve a pH of about 1.5.

Example 8 was a solution of 5 wt. % aminoguanidine-HCl in water, to which 12 N hydrochloric acid had been added to achieve a pH of about 1.5.

Example 9 was a solution of 70 wt. % ethanol and 2 wt. % aminoguanidine-HCl in water, to which 12 N hydrochloric acid had been added to achieve a pH of about 1.5.

Example 10 was a solution of 70 wt. % ethanol and 5 wt. % aminoguanidine-HCl in water, to which 12 N hydrochloric acid had been added to achieve a pH of about 2.

Example 11 was a solution of 70 wt. % ethanol in water, to which 12 N hydrochloric acid had been added to achieve a pH of about 5.

Example 12 was a solution of 5 wt. % aminoguanidine-HCl in water, to which 12 N hydrochloric acid had been added to achieve a pH of about 5.

Example 13 was a solution of 70 wt. % ethanol and 5 wt. % aminoguanidine-HCl in water, to which 12 N hydrochloric acid had been added to achieve a pH of about 5.

Figure 3:
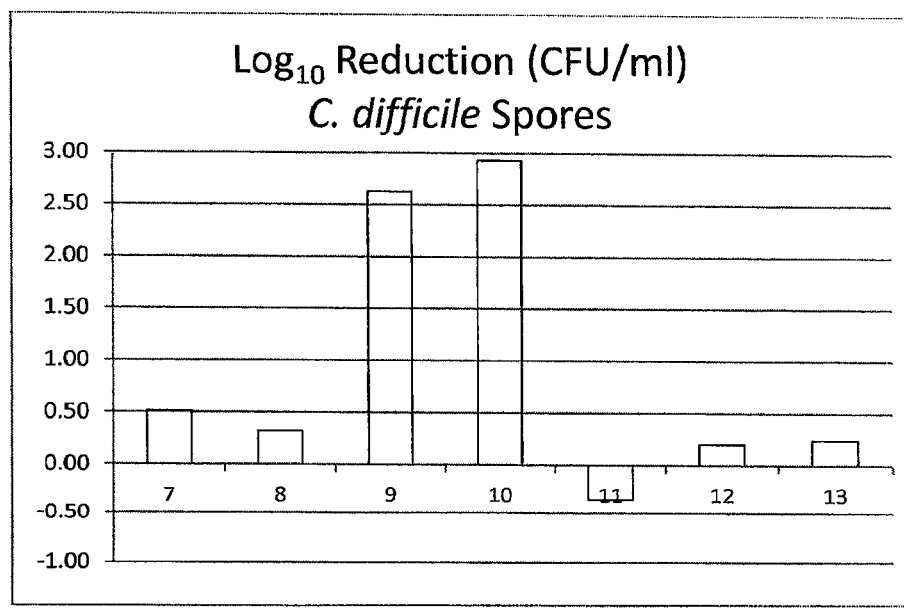
FIG. 3 is a graphical representation of log reduction (CFU/ml) against *C. difficile* spores for test compositions as described herein.

As for Examples 1-4, samples 7-13 were tested for efficacy against *C. difficile* spores, according to the ASTM E2783-11: "Standard Test Method for Assessment of Antimicrobial Activity for Water Miscible Compounds Using a Time-Kill Procedure." Contact time was 30 seconds. Temperature was room temperature. Results are shown in Table 2 and FIG. 3.

TABLE 2

| Example | Composition | pH | $Log_{10}$ Reduction *C. difficile* spores |
|---|---|---|---|
| 7 | 70% ethanol | 1.5 | 0.51 |
| 8 | 5% aminoguanidine-HCl | 1.5 | 0.32 |
| 9 | 70% ethanol + 2% aminoguanidine-HCl | 1.5 | 2.63 |
| 10 | 70% ethanol + 5% aminoguanidine-HCl | 1.5 | >2.93 |
| 11 | 70% ethanol | 5.0 | −0.35 |
| 12 | 5% aminoguanidine-HCl | 5.0 | 0.20 |
| 13 | 70% ethanol + 5% aminoguanidine-HCl | 5.0 | 0.24 |

Example 14 was a solution of 80 wt. % ethanol in water, to which 12 N hydrochloric acid had been added to achieve a pH of about 1.5.

Example 15 was a solution of 80 wt. % ethanol and 2 wt. % aminoguanidine-HCl in water, to which 12 N hydrochloric acid had been added to achieve a pH of about 1.5.

Example 16 was a solution of 80 wt. % ethanol, 2.5 wt. % aminoguanidine-HCl and 2.5 wt % urea in water, to which 12 N hydrochloric acid had been added to achieve a pH of about 1.5.

Example 17 was a solution of 90 wt. % ethanol in water, to which 12 N hydrochloric acid had been added to achieve a pH of about 1.5.

Example 18 was a solution of 90 wt. % ethanol, and 2 wt % aminoguanidine-HC 1 in water, to which 12 N hydrochloric acid had been added to achieve a pH of about 1.5.

Example 19 was a solution of 90 wt. % ethanol, 2.5 wt. % aminoguanidine-HCl and 2.5 wt % urea in water, to which 12 N hydrochloric acid had been added to achieve a pH of about 1.5.

Example 20 was a solution of 80 wt. % ethanol in water, to which 12 N hydrochloric acid had been added to achieve a pH of about 5.

Example 21 was a solution of 80 wt. % ethanol and 2 wt. % aminoguanidine-HCl in water, to which 12 N hydrochloric acid had been added to achieve a pH of about 5.

Example 22 was a solution of 80 wt. % ethanol, 2.5 wt. % aminoguanidine-HCl and 2.5 wt % urea in water, to which 12 N hydrochloric acid had been added to achieve a pH of about 5.

Example 23 was a solution of 90 wt. % ethanol in water, to which 12 N hydrochloric acid had been added to achieve a pH of about 5.

Example 24 was a solution of 90 wt. % ethanol and 2 wt. % aminoguanidine-HCl in water, to which 12 N hydrochloric acid had been added to achieve a pH of about 5.

Example 25 was a solution of 90 wt. % ethanol, 2.5 wt. % aminoguanidine-HCl and 2.5 wt % urea in water, to which 12 N hydrochloric acid had been added to achieve a pH of about 5.

Figure 4:
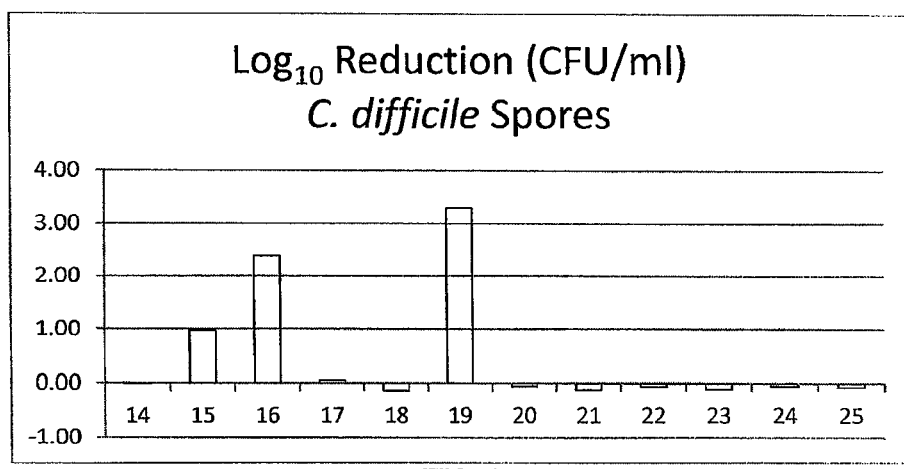
FIG. 4 is a graphical representation of log reduction (CFU/ml) against *C. difficile* spores for test compositions as described herein.

As for Examples 1-4, samples 14-25 were tested for efficacy against *C. difficile* spores, according to the ASTM E2783-11: "Standard Test Method for Assessment of Antimicrobial Activity for Water Miscible Compounds Using a Time-Kill Procedure." Contact time was 30 seconds. Temperature was room temperature. Results are shown in Table 3 and FIG. 4.

TABLE 3

| Example | Composition | pH | $Log_{10}$ Reduction *C. difficile* spores |
|---|---|---|---|
| 14 | 80% ethanol | 1.5 | −0.01 |
| 15 | 80% ethanol + 2% aminoguanidine-HCl | 1.5 | 0.98 |
| 16 | 80% ethanol + 2.5% aminoguanidine-HCl + 2.5% urea | 1.5 | 2.38 |
| 17 | 90% ethanol | 1.5 | 0.05 |
| 18 | 90% ethanol + 2% aminoguanidine-HCl | 1.5 | −0.13 |
| 19 | 90% ethanol + 2.5% aminoguanidine-HCl + 2.5% urea | 1.5 | 3.30 |
| 20 | 80% ethanol | 5.0 | −0.05 |
| 21 | 80% ethanol + 2% aminoguanidine-HCl | 5.0 | −0.12 |
| 22 | 80% ethanol + 2.5% aminoguanidine-HCl + 2.5% urea | 5.0 | −0.06 |
| 23 | 90% ethanol | 5.0 | −0.11 |
| 24 | 90% ethanol + 2% aminoguanidine-HCl | 5.0 | −0.05 |
| 25 | 90% ethanol + 2.5% aminoguanidine-HCl + 2.5% urea | 5.0 | −0.07 |

Example 26 was a solution of 70 wt. % ethanol in water, to which 12 N hydrochloric acid had been added to achieve a pH of about 1.5.

Example 27 was a solution of 70 wt. % ethanol, 0.1 wt. % guanidine-HCl in water, to which 12 N hydrochloric acid had been added to achieve a pH of about 1.5.

Example 28 was a solution of 70 wt. % ethanol and 1 wt. % guanidine-HCl in water, to which 12 N hydrochloric acid had been added to achieve a pH of about 1.5.

Example 29 was a solution of 70 wt. % ethanol and 10 wt. % guanidine-HCl in water, to which 12 N hydrochloric acid had been added to achieve a pH of about 1.5.

As for Examples 1-4, samples 26-29 were tested for efficacy against *C. difficile* spores, according to the ASTM E2783-11: "Standard Test Method for Assessment of Antimicrobial Activity for Water Miscible Compounds Using a Time-Kill Procedure." Contact time was 30 seconds. Temperature was room temperature. Results are shown in Table 4 below.

TABLE 4

| Example | Composition | pH | $Log_{10}$ Reduction *C. difficile* spores |
|---|---|---|---|
| 26 | 70% ethanol | 1.5 | 0.51 |
| 27 | 70% ethanol + 0.1% guanidine | 1.5 | 0.84 |
| 28 | 70% ethanol + 1.0% guanidine | 1.5 | 2.00 |
| 29 | 70% ethanol + 10.0% guanidine | 1.5 | >3.08 |

Example 30 was a simple hand wash.

Example 31 was a solution of 70 wt. % ethanol in water, to which 12 N hydrochloric acid had been added to achieve a pH of about 1.5.

Example 32 was a solution of 70 wt. % ethanol and 10 wt. % urea in water, to which 12 N hydrochloric acid had been added to achieve a pH of about 1.5.

Figure 5:
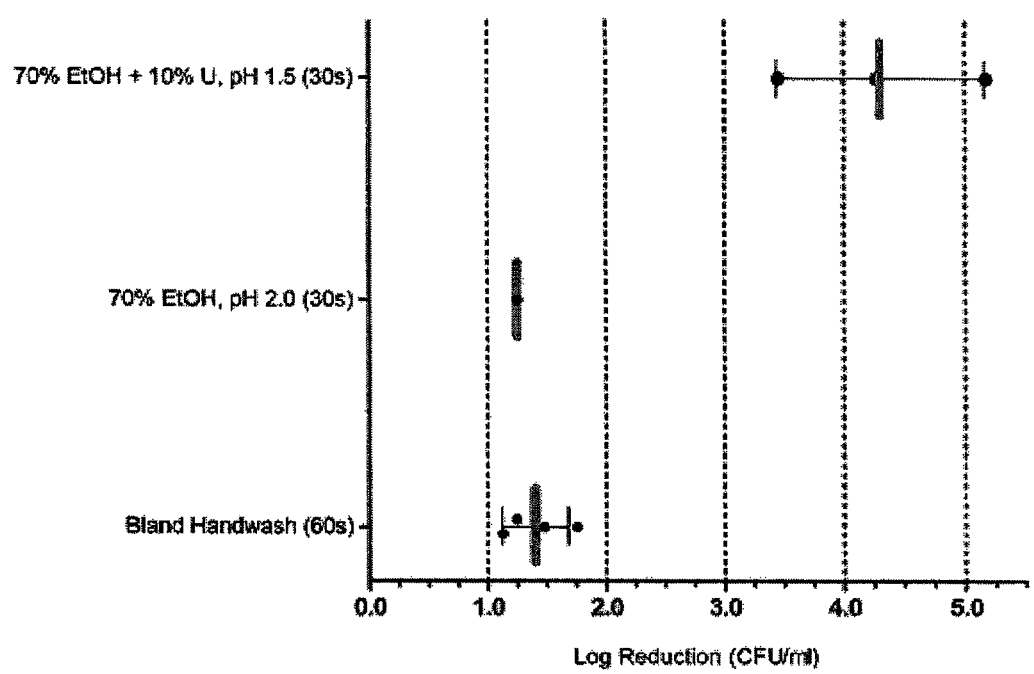
FIG. 5 is a graphical representation of log reduction (CFU/ml) against *C. difficile* spores for test compositions as described herein.

The samples were evaluated at room temperature for efficacy against *C. difficile* spores according to the following In vivo test protocol. Results are shown in Table 5 and FIG. 5.

In Vivo *C. difficile* Spore Test Method Protocol:
Spore Growth Media and Neutralizer
  BPB+: Butterfield's Phosphate Buffer
  BHIT-AMP: Brain Heart Infusion Agar with Sodium Taurocholate hydrate (0.1%) and Ampicillin (0.2 µg/ml)
Inoculum
  Purified *C. difficile* spores (ATCC 700057) at an approximate concentration of 8.5 $\log_{10}$ CFU/ml. Spores were suspended in sterile water and stored at −80° C.
Pretreatment of Hands
  Pre-wash hands with bland soap (GOJO® Clear & Mild Foam Handwash) and pat dry with paper towels and wait five minutes before applying spore inoculum to hands
Inoculation of Fingertips with *C. difficile* Spores
  Dispense 5 µL of the spore suspension directly onto the index, middle, and ring fingerpads of each hand
  Rub opposite fingerpads together on and off until dry
  Wait at least 1 minute before determining the baseline contamination of the fingers
Baseline Recovery
  Sample one finger on each hand separately in standard size petri dishes (100×15 mm) containing 5 mL BPB+ by rubbing for one minute
  Pat fingerpads dry on paper towels to remove excess BPB+
Product Application
  For Handwash: briefly wet hands, apply product (2 pumps of foaming hand washes), lather for 60 seconds, rinse off excess lather for 10 seconds, lightly pat dry
  For disinfectant compositions: (Examples): rub fingertips together under a continuous stream from a wash bottle filled with the appropriate product for the desired exposure time, briefly rinse to neutralize, lightly pat dry
Post Product Exposure Recovery
  Sample index, middle, and ring fingers of each hand together as described above
Enumeration of *C. difficile*
  Dilute baseline and post product exposure recovery in BPB+ and enumerate on BHIT-AMP.
Log Reduction Calculation
  After enumeration of viable *C. difficile* with subtract post exposure recovery from baselines to get a log reduction

TABLE 5

| Example | Composition | pH | Application Time (s) | $\log_{10}$ Reduction *C. difficile* spores |
|---|---|---|---|---|
| 30 | bland handwash | — | 60 | 1.40 |
| 31 | 70% ethanol | 2.0 | 30 | 1.25 |
| 32 | 70% ethanol + 10% urea | 1.5 | 30 | 4.39 |

Example 33 was a solution of 70 wt. % ethanol in water.
Example 34 was a solution of 70 wt. % ethanol and 10 wt. % urea in water, to which 12 N hydrochloric acid had been added to achieve a pH of about 1.5.
Example 35 was a solution of 70 wt. % ethanol and 1 wt. % urea in water, to which 12 N hydrochloric acid had been added to achieve a pH of about 1.5.
Example 36 was a solution of 70 wt. % ethanol and 10 wt. % urea in water, to which 12 N hydrochloric acid had been added to achieve a pH of about 3.
The samples were evaluated for efficacy against *C. difficile* spores according to the following in vivo test protocol.
In Vivo *C. difficile* Spore Test Method Protocol:
Spore Growth Media and Neutralizer
  BPB+: Butterfield's Phosphate Buffer
  BHIT-AMP: Brain Heart Infusion Agar with Sodium Taurocholate hydrate (0.1%) and Ampicillin (0.2 µg/ml)
Inoculum
  Purified *C. difficile* spores (ATCC 700057) at an approximate concentration of 8.5 $\log_{10}$ CFU/ml. Spores were suspended in sterile water and stored at −80° C.
Pretreatment of Hands
  Pre-wash hands with bland soap (GOJO® Clear & Mild Foam Handwash) and pat dry with paper towels and wait five minutes before applying spore inoculum to hands
Inoculation of Fingertips with *C. difficile* Spores
  Dispense 5 µL of the spore suspension directly onto the index, middle, and ring fingerpads of each hand
  Rub opposite fingerpads together on and off until dry
  Wait at least 1 minute before determining the baseline contamination of the fingers
Baseline Recovery
  Sample one finger on each hand separately in standard size petri dishes (100×15 mm) containing 5 mL BPB+ by rubbing for one minute
  Pat fingerpads dry on paper towels to remove excess BPB+
Product Application
  Briefly wet hands, apply product (approximately 3 ml), rub hands together to spread product over hands, and continue rubbing until product has evaporated.
Post Product Exposure Recovery
  Sample index, middle, and ring fingers of each hand together as described above
Enumeration of *C. difficile*
  Dilute baseline and post product exposure recovery in BPB+ and enumerate on BHIT-AMP.
Log Reduction Calculation
  After enumeration of viable *C. difficile* with subtract post exposure recovery from baselines to get a log reduction. Results are summarized in the table below.

TABLE 6

| Example | Composition | pH | Application Volume (ml) | $\log_{10}$ Reduction *C. difficile* spores |
|---|---|---|---|---|
| 33 | 70% ethanol | — | 3.00 | 0.24 |
| 34 | 70% ethanol + 10% urea | 1.5 | 3.00 | 3.58 |
| 35 | 70% ethanol + 1.0% urea | 1.5 | 3.00 | 3.87 |
| 36 | 70% ethanol + 10% urea | 3.0 | 3.00 | 1.00 |

Example 37 was a solution of 70 wt. % isopropanol and 1 wt. % urea in water, to which 12 N hydrochloric acid had been added to achieve a pH of about 1.5.
Example 38 was a solution of 70 wt. % isopropanol and 10 wt. % urea in water, to which 12 N hydrochloric acid had been added to achieve a pH of about 1.5.
Example 39 was a solution of 70 wt. % isopropanol and 1 wt. % urea in water, to which 12 N hydrochloric acid had been added to achieve a pH of about 1.5.
Example 40 was a solution of 70 wt. % isopropanol and 10 wt. % urea in water, to which 12 N hydrochloric acid had been added to achieve a pH of about 1.5.
Example 41 was a solution of 70 wt. % isopropanol and 1 wt. % urea in water, to which 12 N hydrochloric acid had been added to achieve a pH of about 5.

Example 42 was a solution of 70 wt. % isopropanol and 10 wt. % urea in water, to which 12 N hydrochloric acid had been added to achieve a pH of about 5.

Example 43 was a solution of 70 wt. % isopropanol and 1 wt. % urea in water, to which 12 N hydrochloric acid had been added to achieve a pH of about 5.

Example 44 was a solution of 70 wt. % isopropanol and 10 wt. % urea in water, to which 12 N hydrochloric acid had been added to achieve a pH of about 5.

Example 45 was a solution of 70 wt. % n-propanol and 1 wt. % urea in water, to which 12 N hydrochloric acid had been added to achieve a pH of about 1.5.

Example 46 was a solution of 70 wt. % n-propanol and 10 wt. % urea in water, to which 12 N hydrochloric acid had been added to achieve a pH of about 1.5.

Example 47 was a solution of 70 wt. % n-propanol and 1 wt. % urea in water, to which 12 N hydrochloric acid had been added to achieve a pH of about 1.5.

Example 48 was a solution of 70 wt. % n-propanol and 10 wt. % urea in water, to which 12 N hydrochloric acid had been added to achieve a pH of about 1.5.

Example 49 was a solution of 70 wt. % n-propanol and 1 wt. % urea in water, to which 12 N hydrochloric acid had been added to achieve a pH of about 5.

Example 50 was a solution of 70 wt. % n-propanol and 10 wt. % urea in water, to which 12 N hydrochloric acid had been added to achieve a pH of about 5.

Example 51 was a solution of 70 wt. % n-propanol and 1 wt. % urea in water, to which 12 N hydrochloric acid had been added to achieve a pH of about 5.

Example 52 was a solution of 70 wt. % n-propanol and 10 wt. % urea in water, to which 12 N hydrochloric acid had been added to achieve a pH of about 5.

As for Examples 1-4, samples 37-52 were tested for efficacy against *C. difficile* spores, according to the ASTM E2783-11: "Standard Test Method for Assessment of Antimicrobial Activity for Water Miscible Compounds Using a Time-Kill Procedure." Contact time was 30 seconds or 60 seconds, as indicated in the graph below. Temperature was room temperature. Results are shown in the table below.

TABLE 7

| Example | Composition | pH | Exposure time | $Log_{10}$ Reduction *C. difficile* spores |
|---|---|---|---|---|
| 37 | 70% isopropanol + 1% urea | 1.5 | 30 | −0.77 |
| 38 | 70% isopropanol + 10% urea | 1.5 | 30 | 3.31 |
| 39 | 70% isopropanol + 1% urea | 1.5 | 60 | −0.33 |
| 40 | 70% isopropanol + 10% urea | 1.5 | 60 | >3.46 |
| 41 | 70% isopropanol + 1% urea | 5.0 | 30 | −0.37 |
| 42 | 70% isopropanol + 10% urea | 5.0 | 30 | −0.38 |
| 43 | 70% isopropanol + 1% urea | 5.0 | 60 | −0.38 |
| 44 | 70% isopropanol + 10% urea | 5.0 | 60 | −0.14 |
| 45 | 70% n-propanol + 1% urea | 1.5 | 30 | 0.26 |
| 46 | 70% n-propanol + 10% urea | 1.5 | 30 | >3.46 |
| 47 | 70% n-propanol + 1% urea | 1.5 | 60 | 0.67 |
| 48 | 70% n-propanol + 10% urea | 1.5 | 60 | 3.31 |
| 49 | 70% n-propanol + 1% urea | 5.0 | 30 | −0.06 |
| 50 | 70% n-propanol + 10% urea | 5.0 | 30 | 0.18 |
| 51 | 70% n-propanol + 1% urea | 5.0 | 60 | 0.10 |
| 52 | 70% n-propanol + 10% urea | 5.0 | 60 | 0.18 |

Example 53 was a solution of 70 wt. % ethanol and 1 wt. % thiourea in water, to which 12 N hydrochloric acid had been added to achieve a pH of about 1.5.

Example 54 was a solution of 70 wt. % ethanol and 10 wt. % thiourea in water, to which 12 N hydrochloric acid had been added to achieve a pH of about 1.5.

Example 55 was a solution of 70 wt. % ethanol and 1 wt. % guanidine thiocyanate in water, to which 12 N hydrochloric acid had been added to achieve a pH of about 1.5.

Example 56 was a solution of 70 wt. % ethanol and 10 wt. % guanidine thiocyanate in water, to which 12 N hydrochloric acid had been added to achieve a pH of about 1.5.

Example 57 was a solution of 70 wt. % ethanol and 1 wt. % L-N$^G$-Nitroarginine in water, to which 12 N hydrochloric acid had been added to achieve a pH of about 1.5.

As for Examples 1-4, samples 53-57 were tested for efficacy against *C. difficile* spores, according to the ASTM E2783-11: "Standard Test Method for Assessment of Antimicrobial Activity for Water Miscible Compounds Using a Time-Kill Procedure." Contact time was 30 seconds. Temperature was room temperature. Results are shown in the table below.

TABLE 8

| Example | Composition | pH | $Log_{10}$ Reduction *C. difficile* spores |
|---|---|---|---|
| 53 | 70% ethanol + 1% thiourea | 1.5 | >2.90 |
| 54 | 70% ethanol + 10% thiourea | 1.5 | 2.75 |
| 55 | 70% ethanol + 1% guanidine thiocyanate | 1.5 | >2.90 |
| 56 | 70% ethanol + 10% guanidine thiocyanate | 1.5 | 2.51 |
| 57 | 70% ethanol + 1% L-NG-Nitroarginine* | 1.5 | >2.90 |

*CAS # for this molecule: 2149-70-4

Example 58 was a solution of 70 wt. % ethanol in water, to which 12 N hydrochloric acid had been added to achieve a pH of about 3.

Example 59 was a solution of 70 wt. % ethanol and 10 wt. % urea in water, to which 12 N hydrochloric acid had been added to achieve a pH of about 3.

Example 60 was a solution of 70 wt. % ethanol in water, to which 12 N hydrochloric acid had been added to achieve a pH of about 7.

Example 61 was a solution of 70 wt. % ethanol and 10 wt. % urea in water, to which 12 N hydrochloric acid had been added to achieve a pH of about 7.

As for Examples 1-4, samples 58-61 were tested for efficacy against *C. difficile* spores, according to the ASTM E2783-11: "Standard Test Method for Assessment of Antimicrobial Activity for Water Miscible Compounds Using a Time-Kill Procedure." Contact time was 5 minutes. Temperature was room temperature. Results are shown in the table below.

TABLE 9

| Example | Composition | pH | Exposure time (min.) | $Log_{10}$ Reduction *C. difficile* spores |
|---|---|---|---|---|
| 58 | 70% ethanol | 3 | 5 | 0.04 |
| 59 | 70% ethanol + 10% urea | 3 | 5 | 3.14 |
| 60 | 70% ethanol | 7 | 5 | −0.35 |
| 61 | 70% ethanol + 10% urea | 7 | 5 | 0.10 |

Example 62 was a solution of 70 wt. % ethanol in water, to which 12 N hydrochloric acid had been added to achieve a pH of about 2.

Example 63 was a solution of 70 wt. % ethanol, 10 wt. % urea and 1% NaNO$_2$ in water, to which 12 N hydrochloric acid had been added to achieve a pH of about 2.

Example 64 was a solution of 80 wt. % ethanol in water, to which 12 N hydrochloric acid had been added to achieve a pH of about 3.

Example 65 was a solution of 70 wt. % ethanol, 10 wt. % urea, and 1% NaNO$_2$ in water, to which 12 N hydrochloric acid had been added to achieve a pH of about 3.

Example 66 was a solution of 70 wt. % ethanol, 10 wt. % urea, and 1 wt. % tannic acid in water, to which 12 N hydrochloric acid had been added to achieve a pH of about 2.

Example 67 was a solution of 70 wt. % ethanol, 10 wt. % urea, and 1 wt. % citric acid in water, to which 12 N hydrochloric acid had been added to achieve a pH of about 2.

Example 68 was a solution of 70 wt. % ethanol, 10 wt. % urea, and 1 wt. % lauric acid in water, to which 12 N hydrochloric acid had been added to achieve a pH of about 2.

Example 69 was a solution of 70 wt. % ethanol, 10 wt. % urea, and 0.1 wt. % sodium dodecyl sulfate (SDS) in water, to which 12 N hydrochloric acid had been added to achieve a pH of about 3.

Example 70 was a solution of 70 wt. % ethanol, 10 wt. % urea, and 1 wt. % SDS in water, to which 12 N hydrochloric acid had been added to achieve a pH of about 3.

Example 71 was a solution of 70 wt. % ethanol and 1 wt. % sodium laureth sulfate (SLES) in water, to which 12 N hydrochloric acid had been added to achieve a pH of about 1.5.

Example 72 was a solution of 70 wt. % ethanol and 5 wt. % sodium lauryl sulfate (SLS) in water, to which 12 N hydrochloric acid had been added to achieve a pH of about 3.

As for Examples 1-4, samples 62-72 were tested for efficacy against *C. difficile* spores, according to the ASTM E2783-11: "Standard Test Method for Assessment of Antimicrobial Activity for Water Miscible Compounds Using a Time-Kill Procedure." Temperature was room temperature. Results are shown in the table below.

TABLE 10

| Example | Composition | pH | Exposure time (sec) | Log$_{10}$ Reduction *C. difficile* spores |
|---|---|---|---|---|
| 62 | 70% ethanol | 2 | 30 | −0.13 |
| 63 | 70% ethanol + 10% urea + 1% NaNO$_2$ | 2 | 30 | >3.0 |
| 64 | 80% ethanol | 3 | 30 | −0.09 |
| 65 | 70% ethanol + 10% urea + 1% NaNO$_2$ | 3 | 30 | >3.0 |
| 66 | 70% ethanol + 10% urea + 1% tannic acid | 2 | 30 | 3.29 |
| 67 | 70% ethanol + 10% urea + 1% citric acid | 2 | 30 | 3.13 |
| 68 | 70% ethanol + 10% urea + 1% lauric acid | 2 | 30 | 3.13 |
| 69 | 70% ethanol + 10% urea + 0.1% SDS | 3 | 30 | 2.44 |
| 70 | 70% ethanol + 10% urea + 1% SDS | 3 | 30 | >3.13 |
| 71 | 70% ethanol + 1% SLES | 1.5 | 60 | >2.9 |
| 72 | 70% ethanol + 5% SLS | 1.5 | 30 | 1.87 |

Example 73 was a solution of 70 wt. % ethanol in water, to which 12 N hydrochloric acid had been added to achieve a pH of about 1.5.

Example 74 was a solution of 70 wt. % ethanol and 0.25 wt. % NaCl in water, to which 12 N hydrochloric acid had been added to achieve a pH of about 1.5.

Example 75 was a solution of 70 wt. % ethanol and 0.1 wt. % Trilon M in water, to which 12 N hydrochloric acid had been added to achieve a pH of about 1.5.

Example 76 was a solution of 70 wt. % ethanol and 0.5 wt. % Trilon M in water, to which 12 N hydrochloric acid had been added to achieve a pH of about 1.5.

Example 77 was a solution of 70 wt. % ethanol and 1 wt. % Trilon M in water, to which 12 N hydrochloric acid had been added to achieve a pH of about 1.5.

Example 78 was a solution of 70 wt. % ethanol and 2 wt. % Trilon M in water, to which 12 N hydrochloric acid had been added to achieve a pH of about 1.5.

Example 79 was a solution of 70 wt. % ethanol, 0.25 wt. % NaCl, and 1 wt. % Trilon M in water, to which 12 N hydrochloric acid had been added to achieve a pH of about 1.5.

Example 80 was a solution of 70 wt. % ethanol, 0.25 wt. % NaCl, and 2 wt. % Trilon M in water, to which 12 N hydrochloric acid had been added to achieve a pH of about 1.5.

As for Examples 1-4, samples 73-80 were tested for efficacy against *C. difficile* spores, according to the ASTM E2783-11: "Standard Test Method for Assessment of Antimicrobial Activity for Water Miscible Compounds Using a Time-Kill Procedure." Temperature was room temperature. Results are shown in the table below.

TABLE 11

| Example | Composition | pH | Exposure Time (s) | Log Reduction *C. difficile* spores |
|---|---|---|---|---|
| 73 | 70% ethanol | 1.50 | 30 | 0.26 |
| 74 | 70% ethanol + 0.25% NaCl | 1.50 | 30 | 1.92 |
| 75 | 70% ethanol + 0.1% Trilon M | 1.50 | 30 | 1.35 |
| 76 | 70% ethanol + 0.5% Trilon M | 1.50 | 30 | 2.02 |
| 77 | 70% ethanol + 1.0% Trilon M | 1.50 | 30 | 3.31 |
| 78 | 70% ethanol + 2.0% Trilon M | 1.50 | 30 | >3.46 |
| 79 | 70% ethanol + 0.25% NaCl + 1.0% Trilon M | 1.50 | 30 | >3.46 |
| 80 | 70% ethanol + 0.25% NaCl + 2.0% Trilon M | 1.50 | 30 | >3.46 |

Example 81 was a solution of 70 wt. % ethanol and 1 wt. % NaCl in water, to which 12 N hydrochloric acid had been added to achieve a pH of about 1.5.

Examples 3, 10, 72 and 81 were tested for efficacy against *C. difficile* spores according to the EPA Standard Operating Procedure for Quantitative Disk Carrier Test method (QCT-2) Modified for Testing Antimicrobial Products Against Spores of *Clostridium difficile* (ATCC 43598) on Inanimate, Hard, Non-porous Surfaces. SOP Number: MB-31-03. Date Revised 6 Dec. 2014, which is incorporated by reference herein. This quantitative method is used to evaluate the sporicidal efficacy of liquid disinfectants against spores of *Clostridium difficile* (ATCC 43598) on inanimate, hard, non-porous surfaces. Results are shown in the table below.

TABLE 12

| Example | pH | Log Reduction *C. difficile* spores At 7 minutes | Log Reduction *C. difficile* spores At 10 minutes |
|---|---|---|---|
| 3 | 1.50 | 6.3 | 6.2 |
| 10 | 1.50 | 6.2 | 6.2 |
| 72 | 1.50 | 6.20 | 6.20 |
| 81 | 1.50 | 6.20 | 6.20 |

Various modifications and alterations that do not depart from the scope and spirit of this invention will become apparent to those skilled in the art. This invention is not to be duly limited to the illustrative embodiments set forth herein.

What is claimed is:

1. A composition for the disinfection of surfaces, the composition comprising:
   at least about 40 wt. % of a $C_{1-6}$ alcohol, based upon the total weight of the composition,
   at least one primary enhancer, and
   optionally, at least one secondary enhancer selected from the group consisting of non-ionic surfactants, organic acids, antimicrobial agents, oxidizing agents, sugars, sugar alcohols, monosaccharides, glycerol and combinations thereof,
   wherein the disinfectant composition is characterized by a pH of less than about 3.

2. The composition of claim 1, wherein the composition exhibits a synergistically enhanced efficacy against bacterial and fungal spores, when compared to the efficacy of the alcohol or primary enhancer alone.

3. The composition of claim 1, wherein the composition exhibits a synergistically enhanced efficacy against *C. difficile* spores, when compared to the efficacy of the alcohol or primary enhancer alone.

4. The composition of claim 1, wherein the primary enhancer is selected from the group consisting of amine-containing enhancers, α-aminoacids, salts of alkali metals, salts of alkaline earth metals, anionic surfactants, and combinations thereof.

5. The composition of claim 4, wherein the amine-containing enhancer is selected from the group consisting of urea, thiourea, guanidine-HCl, guanidine thiocyanate, aminoguanidine bicarbonate, guanidine carbonate, guanidine phosphate, aminoguanidine-HCL, and combinations thereof.

6. The composition of claim 1, wherein the composition comprises at least two secondary enhancers.

7. The composition of claim 1, wherein the at least one secondary enhancer is selected from the group consisting of decyl glucoside, polyalkoxylated dimethicones, glycerol, and combinations thereof.

8. The composition of claim 1, wherein the organic acid is selected from the group consisting of citric acid, lauric acid, tannic acid, and combinations thereof.

9. The composition of claim 1, wherein the antimicrobial agent is selected from the group consisting of triclosan, PCMX, chloroxylenol, hexetidine, chlorhexidine salts 2-bromo-2-nitropropane-1, 3-diol, benzalkonium chloride, cetylpyridinium chloride, alkylbenzyldimethylammonium chlorides, iodine, phenol, bisphenol, diphenyl ether, phenol derivatives, povidone-iodine, parabens, hydantoins and derivatives thereof, phenoxyethanol, cis isomer of 1-(3-chloroallyl)-3,5,6-triaza-1-azoniaadamantane chloride, diazolidinyl urea, benzethonium chloride, methylbenzethonium chloride, glyceryl laurate, transition metal compounds, hydrogen peroxide, chlorine dioxide, anilides, bisguanidines, tropolone, $C_{6-10}$-alkane diols, and combinations thereof.

10. The composition of claim 1, wherein the composition provides a log reduction against spores of at least I when the contact time is from about 30 seconds to about 5 minutes.

11. The composition of claim 1, wherein the primary enhancer includes one or more salts selected from the group consisting of ammonium, calcium, iron, lithium, magnesium, and sodium salts.

12. The composition of claim 11, wherein the primary enhancer is selected from the group consisting of ammonium chloride, ammonium iron citrate, calcium chloride, iron perchlorate, lithium perchlorate, lithium acetate, magnesium chloride, sodium chlorate, sodium chloride, sodium chlorite, 2-amino-2-hydroxy methyl-propane-1,3-diol hydrochloride, and combinations thereof.

* * * * *